United States Patent [19]
Hadzic et al.

[11] Patent Number: 5,910,135
[45] Date of Patent: Jun. 8, 1999

[54] INTRAVENOUS INFUSION SYSTEM

[75] Inventors: Admir Hadzic, Montclair, N.J.; Jerry Darius Vloka, New York, N.Y.

[73] Assignee: Innovative Design Associates, Montclair, N.J.

[21] Appl. No.: 08/823,064

[22] Filed: Mar. 31, 1997

[51] Int. Cl.⁶ .................................................. A61M 5/00
[52] U.S. Cl. ............................................................ 604/251
[58] Field of Search .................................... 604/251, 264, 604/280, 80, 81, 122, 246, 253, 254, 258, 260, 407

[56] References Cited

U.S. PATENT DOCUMENTS

| | | | |
|---|---|---|---|
| 2,969,063 | 1/1961 | Broman | 128/214 |
| 3,298,367 | 1/1967 | Bergman | 128/214 |
| 3,877,428 | 4/1975 | Seagle et al. | 128/214 R |
| 4,175,558 | 11/1979 | Hess, III et al. | 128/214 C |
| 4,540,403 | 9/1985 | Theeuwes | 604/85 |
| 4,781,698 | 11/1988 | Parren | 604/246 |
| 4,908,019 | 3/1990 | Urquhart et al. | 604/85 |
| 5,019,055 | 5/1991 | O'Boyle | 604/249 |
| 5,318,515 | 6/1994 | Wilk | 604/30 |
| 5,328,487 | 7/1994 | Starchevich | 604/246 |
| 5,429,615 | 7/1995 | Starchevich | 604/246 |

FOREIGN PATENT DOCUMENTS

| | | | |
|---|---|---|---|
| 1125134 | 6/1982 | Canada | 128/91 |

*Primary Examiner*—John D. Yasko
*Assistant Examiner*—Manuel Mendez
*Attorney, Agent, or Firm*—Fitch, Even, Tabin & Flannery

[57] ABSTRACT

The present invention is directed to an intravenous fluid infusion system that includes a dual-sight drip chamber. The infusion system allows for improved, inexpensive and convenient administration of IV fluids during anesthesia and surgery, using the principles with which practicing anesthesia providers are most comfortable with.

6 Claims, 2 Drawing Sheets

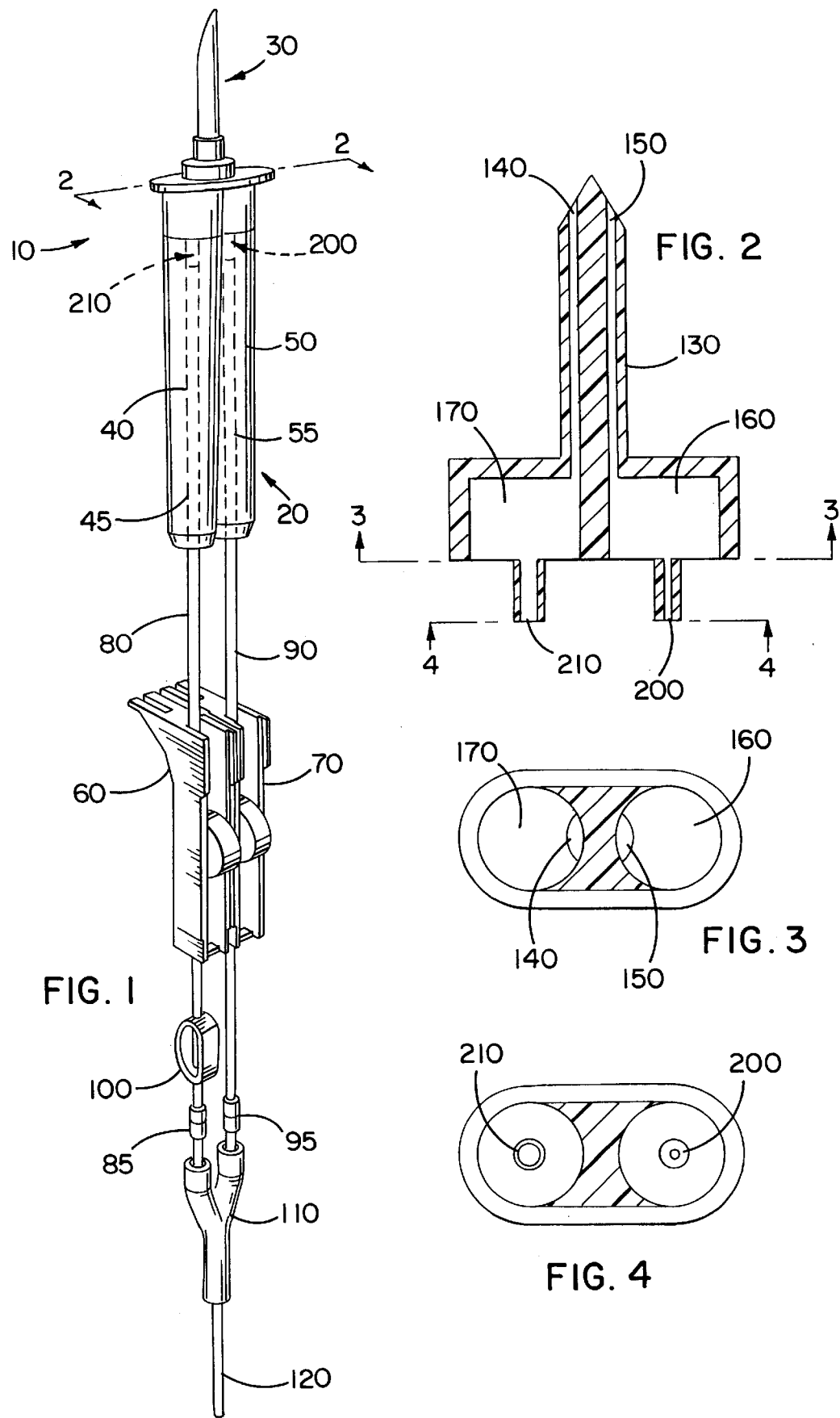

INTRAVENOUS INFUSION SYSTEM

The present invention relates to an intravenous fluid infusion system designed for safe and convenient administration of IV fluids during anesthesia and surgery. More particularly, the system includes a dual-sight drip chamber that allows for independent and simultaneous control and monitoring of intravenous fluid administration in each of two fluid paths.

BACKGROUND OF THE INVENTION

Intravenous (IV) administration of fluids and drugs is an integral part of the routine care of patients, especially those undergoing anesthesia and surgery. Every year in the United States, some 20 million patients undergo surgery and anesthesia. IV infusion is essential as a route of drug administration during induction and maintenance of anesthesia throughout surgical or other procedures.

During administration of anesthesia, invariably there is a need for administration of IV fluids using variable flow rates. In addition to providing a basal infusion rate (maintenance IV fluids), there is a need for frequent intravenous administration of different anesthetic or other medications in boluses. While it is important that these medications are carried into the cannulated vein by a continuous IV flow, administration of excess quantities of IV fluids is frequently undesirable, or deleterious. It follows that a moderately slow and flow-adjustable IV delivery system is preferred. However, ongoing blood or intravascular volume losses, or cardiovascular instability due to occasionally profound general or regional anesthesia, allergic reactions or intravascular volume redistribution, can create the need for quick delivery of larger fluid boluses or faster infusion rates in order to support the circulation. Fluid loading or replacements are frequently administered with great immediacy during various surgical or interventional procedures.

The most commonly used IV infusion system consists of a bag filled with IV fluids, a drip chamber, roller clamp (variable resistance controller) for control of the flow and tubing connected to an IV catheter. The elevated IV bag in this system serves as a pressure source, the roller clamp as a user-controlled resistor, and the IV catheter as a fixed resistor.

Most commonly, the rate of IV fluids flow is determined by the rate at which drops of liquid are observed falling through a drip chamber. Gravity infusion of the parenteral solution is accomplished by suspending the solution container several feet above the patient and connecting the solution container to the venopuncture site via a disposable intravenous administration set which includes a drip chamber and flexible delivery tube.

Flow rates (drops/ml/min) are controlled by use of a roller clamp. U.S. Pat. No. 4,175,558 describes a roller clamp for collapsing the delivery tube to control the flow rate. The roller clamp is a simple, inexpensive, two-piece plastic device that progressively compresses the plastic tube of the intravenous administration set at a single point on the tube thereby occluding the tube to create a pressure drop across the restriction and a corresponding reduction in flow rate. Although the constancy of flow rates during use of such roller clamps is problematic due to cold flow or creep of the plastic tubing at the point of restriction, which causes the flow rate to decrease after setting, this problem is of negligible clinical importance in anesthesia practice. This is so, because the anesthesia provider by the nature of the profession repeatedly has to check and adjust the flow rate according to the clinical circumstances or phases of the anesthetic course.

Continuous flow through the infusion system is usually necessary to ensure the proper delivery of the injected drugs into the patient and avoid accumulation of repeated doses within the IV tubing. However, administration of excess IV fluids is undesirable and frequently harmful. Even in otherwise healthy patients, inadvertently administered large volumes of IV fluids can result in urinary bladder distention and need for urethral catheterization during the surgery, or urinary obstruction post-operatively, all of which can cause delays in discharge. In patients with heart or lung disease, the administration of excessive fluid volumes is a frequent cause of postoperative lung and cardiovascular dysfunction. This can result in congestive heart failure, pulmonary edema (swelling of the lungs) and difficulties in discontinuing mechanical ventilation (breathing machine) after surgery and anesthesia.

While the administration of IV fluids is commonly controlled using "microdrip" IV infusion systems (60 drops/ml), which provide reliably slow infusion rates, these systems are not suitable for administration of fluid boluses and emergent intravascular expansion or replacement of ongoing surgical volume losses should that become necessary (blood loss, syncope, allergic reaction to medications or contrast agents, etc.) during the procedure.

On the other hand, the macro-drip infusion systems (15 drops/ml), which are most commonly used in anesthesia, allow for administration of high fluid rates and fluid boluses, but controlling the flow rate is cumbersome and inexact. Since these systems are capable of delivering high flow rates, failure to frequently assess and adjust the infusion rate using a roller clamp can easily result in administration of excess IV fluids, i.e., 1000 ml over 10 min. The risk of administering large fluid volumes is ever present also due to the deficiencies inherent in these infusion systems. For instance, the rate of drip formation has been found to be an inaccurate measure of flow rate because of the influence of temperature, fluid composition, orifice diameter, and orifice shape. Furthermore, the cold flow (creep) in the tubing underlying the roller clamp contributes to flow variation in excess of 15% over 45 minutes. When a vein collapses, critically high flow velocities occurs, causing the distention of the vessels (produced by the downstream resistance) and paradoxically increase in the IV flow. Veins are characterized by an opening pressure and by a small resistance to flow. Tissues behave as ordinary resistors with a resistance higher than that of veins. The opening pressure of tissue usually is no greater than that of veins, at least initially. In tissues, there is no obstructing pressure when there is no extravasation. However, as fluid is infused, opening tissue pressure rises. In response to these changes in flow rates, the clinician frequently has to check and adjust the roller clamp in order to properly adjust the IV flow so that the flow is continuous, keeping the veins open and assuring the delivery of administered medications and anesthetics, but not excessive to result in fluid overload or infusion of inappropriately large quantities of IV fluids.

In addition to the mentioned irregularities in maintaining the steady flow rate, many clinical situations produce venous collapse, resulting in veins and surrounding tissues behaving like Starling resistors and influencing the flow rate. Typical situations include patient positioning, blood pressure cuff inflation, venous tourniquets (or strapping of the patient's arm to an operating table on-board extension), problematic venous sites, catheter against the venous wall, etc. The clinician is unaware of actual resistance provided by the roller clamp. He or she simply moves the roller clamp until proper flow rate is reached (judged by measuring the rate of drop formation).

Thus, when the IV flow ceases in the above situations, the dripping in the chamber also stops. The clinician frequently completely opens the roller clamp in an attempt to restore the IV flow. However, since deflation of the blood cuff, removal of the tourniquet, or patient repositioning restores the flow, so that unless the clinician remembers that he or she intentionally opened the roller clamp and fails to detect restoration of flow in a timely manner, the patient will almost certainly receive a large bolus of fluids. Since the most commonly used IV set in anesthesia, 15 drops/ml ("macrodrip"), is capable of delivering flow rates as high as 75 ml/min through a 20 G (gauge) IV with just a moderate elevation of the IV bag, this situation would result in administration of 750 ml of fluids in just 10 minutes.

Frequent adjustment in the flow rate is important to counteract periodic, potentially large changes in IV flow due to the described interference in which the flow can start and stop even with small changes in bag elevation or patient repositioning. Thus, the administrator is frequently tempted to completely open the roller clamp during the times when the infusion rate is slowed or when there is a need for "flushing" of administered medications or anesthetics into the IV tubing. Failure to notice the increase in flow when the obstruction to the flow is removed, or failure to decrease the flow after the administered medications are flushed, can again, easily result in administration of excess of fluids. This readily occurs during the times when the clinician becomes distracted by performing a procedure or administering anesthesia.

IV systems used in anesthesia and during different procedures (i.e. cardiac catheterization, interventional radiology, GI and pulmonary endoscopies, etc.) are also frequently used as a carrier for administration of sedatives, anesthetics and other medications. Most commonly, drugs are administered from a syringe with the needle into the flowing IV stream that is powered with gravity. Although administration of IV fluids per se may not be needed or even might be undesirable, IV administration of medications requires a free flowing IV stream, which necessarily results in fluids being administered to the patient.

While using a microdrip IV set (60 drops/ml) for this purpose would minimize the possibility of inadvertent administration of large quantities of IV fluids and assure the delivery of injected medications by a slow IV flow, the maximum flow rate through this system is inadequate should the patient become unstable or require emergent IV intervention. On the other hand, macrodrip sets (15 drops/ml) are excellent for resuscitation, but carry the risk of inadvertent infusion of large IV boluses in the above described circumstances. Although theoretically, one can exchange the microdrip system for a macrodrip system if that becomes necessary, this is time consuming since this would be done in urgent situations. Additionally, exchanging the IV sets carries a risk of loosing the existing IV line, should the IV catheter inadvertently become dislodged during the maneuver, which occasionally happens clinically.

Systems for administering intravenous liquids are described in U.S. Pat. No. 3,298,367 and U.S. Pat. No. 5,318,515. The '367 patent describes a plurality of separate flow paths with each flow path having a predetermined flow characteristic. Each path is associated with an on/off element. An even more sophisticated system for administering intravenous fluids is described in the '515 patent. The '515 patent describes a plurality of separate flow paths with each flow path having a predetermined flow characteristic. The flow in each path is controlled by a selector mounted to a housing which allows for setting or selecting a desired flow rate.

In the dynamic environment during operation and delivery of anesthesia, the administration of fluids using the systems described in both the '367 and '515 patents would require a time consuming selection from a finite number of tubes and associated flow characteristics.

Canadian Patent No. 1,125,134 describes an apparatus for administering incompatible I.V. liquids. The '134 apparatus includes two independent parenteral solution chambers with two independent piercing pin assemblies and two independent sight-drip chambers for incompatible liquids. Hence, the user of the '134 system would be required to insert two separate piercing spikes into two separate solution containers. In addition to adding complexity to administering IV fluids, this system is by necessity costlier since two bags with IV fluids are used. Additionally, since these two piercing spikes are separately inserted, they are frequently positioned at different levels above the infusion site. This, in return, results in different gravity driving pressure and can result in difficulty in maintaining a simultaneous flow through both IV paths, or over-spilling of fluids or medications from one path to another. By having the drip chambers in a common enclosure, the present invention prevents these problems.

Several flow rate regulators, such as the Abbott Laboratories' Dial-A-Flow, see U.S. Pat. No. 3,877,428 have been introduced in recent years in attempts to overcome the aforementioned disadvantages associated with the use of conventional roller clamps and infusion procedures. U.S. Pat. No. 5,019,055 is yet another invention designed in order to improve the accuracy of delivering the desired flow rate and is said to represent an advantage of the aforementioned Dial-A-Flow device.

However, since anesthesia providers routinely work in an intense and dynamic environment prone to human mistakes, any unnecessary complexity of the equipment used during administration of anesthesia introduces a risk of a mishap. These systems are also designed to provide a wide range of flow rates through a single drip chamber. Since the capillary tube in this singular drip chamber has to be of a large diameter, this results in a very slow droplet formation when a slow infusion rate is selected. This again, precludes monitoring of the flow rate and prevents the operator from assuring continuous flow by observing the rate of drops formation, which is the most common and convenient method of monitoring of IV flow used by anesthesiologists. The ability to observe flow rate and adjust it accordingly is far more important in anesthesia practice than the limitation of flow provided by these infusion devices. Consequently, none of these devices have been widely accepted in anesthesia practice. Thus, the present invention also provides a means of avoiding the mixing or flow from one path to another by having separate drip chambers and flow paths at the same height in one enclosure.

It is an object of the present invention to provide an infusion system that corresponds to the conventional droplet monitoring technique and will, therefore, be acceptable to medical practitioners.

Another object of the invention is to provide an infusion system that permits the user to quickly and easily adjust flow rates in accordance with the observed clinical response of the patient receiving the fluids.

Another object of the invention is to provide an infusion system that is inexpensive to manufacture.

Another object of the invention is to provide a sterilized kit containing an infusion system for the administration of intravenous fluids.

Another object of the invention is to provide a simple and easy method for administration of intravenous fluid.

SUMMARY OF THE INVENTION

The infusion system of the present invention permits accurate adjustment and maintenance of flow rates using only a small number of simple, low cost parts. A dual-sight drip chamber provides a conventional droplet monitoring system that is familiar to medical practitioners. Further, the infusion system allows a user in a dynamic environment to easily and accurately control intravenous fluid administration based on clinical response to fluid infusion. The infusion system provides the user with considerable flexibility to respond, as a microdrip flow path provides a continuous flow that allows a vein to be kept open continuously, while a macrodrip flow is available for administration of large flow volumes as needed. The simplicity of the system provides for simple construction and consequently reduced manufacturing costs, making the system highly desirable as a disposable intravenous administration system.

The present invention provides an infusion system for intravenous administration of fluid to a patient from a fluid reservoir. The infusion system includes a supply tube assembly effective for dividing a flow of fluid from the fluid reservoir into a macroflow path and a microflow path. The macroflow and microflow paths flow into a dual-sight drip chamber. The dual-sight drip chamber includes a separate macrodrip chamber and a separate microdrip chamber. Fluid flow from the dual-sight drip chamber is regulated by a flow control device effective for regulating flow of fluid in the macrodrip path and a flow control device effective for regulating flow of fluid in the microdrip path. A clamp is included in the macrodrip path that is effective for instantaneous and complete interruption of the flow of IV fluids in the macrodrip path. The macroflow path and microflow path are joined into a single flow by a junction which is effective for receiving and joining the flow paths. The infusion system of the present invention is intended for use for purpose of administering fluids and anesthetics during anesthesia and surgery However, it is also ideal for use in different procedure locations such as emergency rooms, gastroscopy, endoscopy suites, cardiac catheterizatlon labs, pulmonary units, as well as in a general medical ward.

Other aspects, advantages, features and characteristics of the present invention will become more apparent upon consideration of the following description and the appended claims.

BRIEF DESCRIPTION OF THE DRAWINGS

FIG. 1 shows a perspective view of a system for the infusion of intravenous fluids according to the present invention.

FIG. 2 shows a cross-sectional view of a supply tube assembly used in the in system of the present invention as taken along lines 2—2 in FIG. 1.

FIG. 3 shows a bottom-plan view of the supply tube assembly shown in FIG. 2 as taken along line 3—3 of FIG. 2.

FIG. 4 shows a bottom-plan view of the supply tube assembly taken along line 4—4 of FIG. 2.

DETAILED DESCRIPTION OF THE INVENTION

Figure 5:
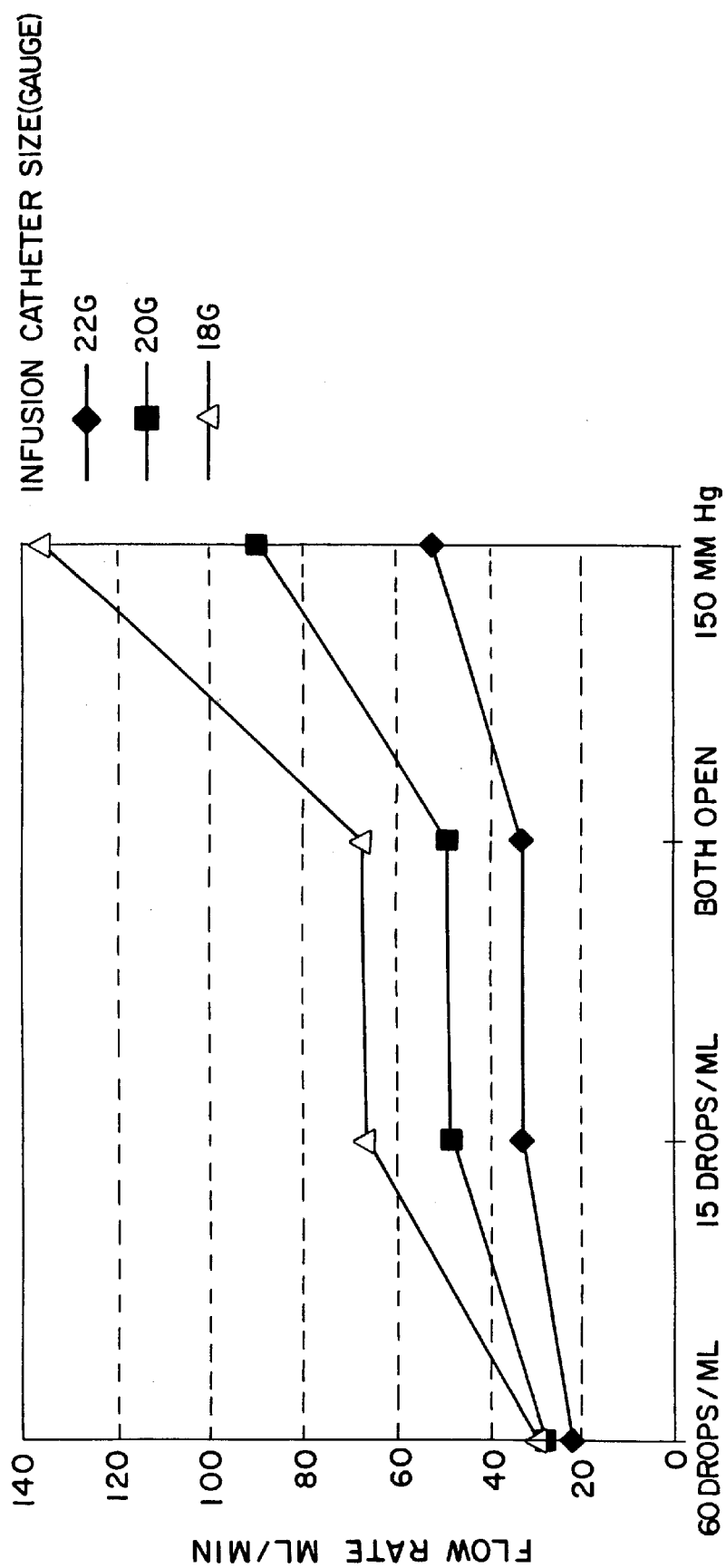
FIG. 5 shows the infusion characteristics of the dual sight drip chamber infusion system. The fluid rates shown are with the roller clamp completely opened and with the air-fluid level in the IV bag elevated 100 cm above the IV access level. The figure shows gravity driven flow rates through a 15 drops/ml fluid chamber, 60 drops/ml fluid chamber or both fluid paths simultaneously through 22, 20 or 18 gauge catheters. The 150 mmHg refers to a flow rate when a pressure of 150 mmHg is applied over the IV bag to increase the flow rate as it is occasionally done in various clinical conditions requiring very high flow rates. The flow shown after application of pressure to the bag is through both fluid paths.

Referring now specifically to the drawings, and the illustrative embodiments depicted therein, FIG. 1 shows an infusion system 10. The infusion system 10 has a fluid reservoir (not shown), preferably of the collapsible bag type, that is supported above a patient by a rack member (not shown). A dual sight drip chamber 20 is connected to the fluid reservoir by a supply tube assembly 30 that punctures and extends into the reservoir. The supply tube assembly 30 divides the flow of liquid from the reservoir into two separate paths, a macroflow path 45 and a microflow path 55, such that one path flows into and through a macrodrip chamber 40 and one into and through a microdrip chamber 50 of the dual sight drip chamber 20. The supply tube assembly may have a venting mechanism (not shown) incorporated. Flow control devices 60 and 70, illustratively shown as roller clamps, are connected to the chambers of the dual sight drip chamber 20 by tubing or conduit 80 and 90. The tube 80 that originates from the macrodrip chamber 40 includes a clamp 100 that is effective for completely stopping flow of liquid through the tube 80 and for completely stopping the flow of liquid through the macroflow path 45. The flow from tubes 80 and 90 is joined together into a common path by a junction 110. Both tubes, 80 and 90 have standard one way sterilizable valves 85 and 95 in their path just before junction 110. While the same level of suspension of the macro and microdrip chambers prevents the cross-flow between the two paths, these valves prevent back-flow. The junction 110 is connected to a feed tube 120 that is configured for insertion into the hub of a needle or intravenous catheter inserted into the patient's vein. Substantially, all of the above components are made of elastomeric material and tubings of standard size typically utilized for medical applications. All connections are fluid-tight as effected by procedures commonly utilized in the art. The components are packaged in a sterilized kit and are disposable after use.

The Dual-Sight Drip Chamber

The dual sight drip chamber 20 is transparent, and in an important aspect of the invention is made from clear-plastic materials which are capable of being sterilized by procedures commonly utilized for sterilizing medical equipment and devices. The dual sight drip chamber 20 is used to trap air, and it is used in cooperation with flow control devices 60 and 70 and clamp 100, for adjusting the rate of flow of medical fluids dropwise through the system. Since the dual sight drip chamber is transparent, the user can visually regulate the flow of liquid in both chambers and visually verify that the flow of liquid is occurring and has not been interrupted.

The dual sight drip chamber is divided into two separate chambers, a microdrip chamber 50 and a macrodrip chamber 40. The outside walls of the two chamber can be fixed to each other using techniques known in the art.

The distance from the top to the base of the dual sight drip chamber 20 is about 50 mm to about 70 mm, and in a preferred embodiment is about 60 mm. When the microdrip chamber 50 and macrodrip chamber 40 are positioned next to each other as shown in FIG. 1, the diameter of both chambers together is about 25 to about 35 mm, and in a preferred embodiment is about 30 mm. Each chamber (macrodrip chamber 40 and microdrip chamber 50) has a volume capacity of from about 5 ml to about 10 ml.

The microdrip chamber

The microdrip chamber 50 provides a steady, slow infusion rates for keeping the veins patent and to insure the delivery of medications that are administered either as continuous infusions or as boluses. The microdrip chamber 50 receives fluid from supply tube assembly 30 and through the microflow passage 160 which is in a fluid-tight connection with the top portion of the microdrip chamber 50. Tube 90 extends from the microdrip chamber 50. Roller clamp 70, disposed on tube 90, is used in connection with microdrip chamber 50 to regulate the flow rate of the fluid and provide a continuous microflow path 55. Even if an obstruction to the IV flow requires complete opening of the microdrip roller clamp 70, there is only a minimal chance of fluid overload should the resistance to the flow suddenly decrease since the maximal flow rate through the microdrip chamber is substantially less than that of various macro-drips (i.e., 15 drops/ml), which are commonly used in the practice of anesthesiology. In an important aspect of the invention, the microdrip chamber 50 is typically operated at low flow rates of about 30 drops/minute to fully opened. This amounts to IV fluid flow rates from only about 0.5 ml/min (60 drops/ml) to a maximal fluid flow of about 28 ml/min with the roller clamp fully opened, an 18 G catheter attached to the infusion end, and the air-fluid level raised to 100 cm above the infusion site (see FIG. 5).

The macrodrip chamber

The macrodrip chamber 40 receives fluid from supply tube assembly 30 and through the macroflow passage 170 which is in a fluid-tight connection with the top portion of the macrodrip chamber 40. Tube 80 extends from the macrodrip chamber 40. Roller clamp 60, disposed on tube 80, is used in connection with microdrip chamber 50 to regulate the flow rate of the fluid. The macrodrip chamber 40 can be kept closed off with a clamp 100. When, or if the need for fluid replacement arises, clamp 100 can be released to allow for rapid flow rates through the macrodrip chamber. After clamp 100 is opened, macrodrip roller clamp 60 can be left wide open for rapid administration of IV fluid boluses or controlled to allow for faster infusion rates as a compensation to intraoperative bleeding, etc. In an important aspect of the invention, the macrodrip chamber 40 is typically operated at flow rates of from about 60 drops/min to fully open. This amounts to an IV fluid flow rate of about 4 ml/min (15 drops/ml) to maximal fluid flow of approximately 75 ml/min with the roller clamp fully opened, and 18 G catheter attached to the infusion end, and the air-fluid level raised to 100 cm above the infusion site (see FIG. 5).

The Supply Tube Assembly

In an important aspect of the invention, the supply tube assembly 30 is effective for dividing the flow of fluid from the fluid reservoir into a macroflow path 45 (shown by the dotted lines in FIG. 1) and a microflow path 55 (shown by the dotted lines in FIG. 1). Supply tube assembly 30 is shown in more detail in FIGS. 2, 3 and 4.

As shown in FIG. 2, the supply tube assembly 30 includes a spike connector 130. The spike connector 130 is used to puncture and extend into a fluid reservoir bag (not shown). In an important aspect, the spike connector 130 punctures and extends into a single common reservoir or reservoir bag. The diameter of the spike connector is about 3 mm to about 6 mm.

The spike connector 130 includes two separate flow channels, a microchannel 150 and a macrochannel 140, which are effective for dividing the fluid flow from the reservoir into two paths, a microflow path 55 and a macroflow path 45. Each microchannel has a diameter of about 1.0 mm to about 2.0 mm.

Microchannel 150 and macrochannel 140 conduct fluid to a microflow passage 160 and a macroflow passage 170, respectively, both of which are located at the base of supply tube assembly 30. Each microflow passage has a diameter of about 15 mm to about 20 mm, and preferably about 17 mm. In an important aspect of the invention, the microdrip chamber and macrodrip chamber are located at the same height (level), which assures equal driving gravity forces through both fluid paths.

FIG. 3 shows an end view of supply tube assembly 30 taken across line 3—3 of FIG. 2. Fluid flows into microflow passage 160 and macroflow passage 170. Attached to microflow passage 160 and macroflow passage 170 are microdrip tube 200 and macrodrip tube 210, respectively (as shown in FIG. 1 and in FIG. 4).

The microdrip tube 200 extends into the microdrip chamber 50 and the macrodrip tube 210 extends into the macrodrip chamber 40. Fluid flows through the supply tube assembly 30 and through the microdrip tubes, such that liquid droplets form at the end of each drip tube and subsequently fall into the macrodrip chamber 40 and microdrip chamber 50. Microdrip tube 200 is of a slightly smaller caliber than macrotube 210.

Flow Control Devices

Flow control devices 60 and 70 are located on tubing 80 and 90 which extend from the macrodrip chamber 40 and the microdrip chamber 50. The flow control devices may be any of those commonly known in the art including a roller clamp as shown in FIG. 1. Flow control devices 60 and 70 may be identical, however, each flow control device may be of a different type. In an important aspect of the invention, each flow control device 60 and 70 allows the user to independently and separately select a full range of flow rates for the macroflow path 45 and the microflow path 55.

In an important aspect of the invention, a clamp 100 is located on tube 80. The clamp 100 is effective for completely stopping the flow of fluid in macroflow path 45.

The Junction

The infusion system includes a junction 110 effective for joining the macroflow path 45 and the microflow path 55 into a single flow path. A supply tube 120 carries the fluid to the patient. The junction 110 may be any type of connector effective to join a flow from two separate tubes and convey that flow into a single tube. In disclosed embodiment of the invention, the tube is typically a standard Y-junction which can be connected by water-tight connections to tubing 80, 90 and supply tube 120. The distance from the base of the dual sight dripchamber 20 to the Y-junction 110 is about 135 mm to about 185 mm, and in an important aspect about 160 mm.

System Operation

The above-described infusion system operates as follows. After the sterile IV set is removed from a sterilized package, the spike connector 130 of the supply tube assembly 30 is spiked into and through the outlet closure of an IV bottle or bag containing IV fluids. Both roller clamps, the microdrip roller 70 and the macrodrip roller 60, and clamp 100 are opened until the I.V. tubing is purged of air and then closed, so that the micro and macrodrip chambers are half-filled with fluids. The upper half of each chamber contains air through which the formed micro and macro droplets fall.

When it is desired to infuse a particular liquid into a patient, a needle or catheter which is connected to the end of the feed tube 120 is inserted in the patient's vein. In an important aspect of the invention, fluid flow through the macrodrip chamber 40 and microdrip chamber 50 can be controlled separately and independently of each other. The desired, slow flow rate through the microdrip chamber 50 is set by using the roller clamp 70 included in this path. This infusion rate is used throughout, monitored by visually observing the rate of drop formation, and adjusted according to clinical circumstances. In most routine anesthetics given, the infusion rates through the microdrip path will be ideal and adequate since the rate is easily controlled and the over administration of fluids is eliminated by relatively low maximal infusion rates through the system. However, if and when higher flow rates, fluid boluses, or flushing of the line are needed, the clamp 100 include in the macroflow path 45 is opened and the rate through the macrodrip chamber 40 is adjusted as needed. When the higher infusion rates through the macrodrip chamber are no longer needed, this path is clamped off and the slow infusion through the microflow path 55 spontaneously resumes at the previously set rate.

In an important aspect of the invention, slow infusion rates set through the microdrip chamber 50 remain reasonably accurate and resume at a preset flow level after the macroflow path 55 is clamped off. This feature effectively reduces or avoids the possibility of fluid overload should the operator become distracted, while providing a slow, steady IV flow rate.

Infusion Kit

In an important aspect of the invention, the infusion system of the present invention can be packaged into a set or kit. The packaged kit includes a supply tube assembly 30, a dual-sight drip chamber 20, tubing 80 containing an internal one way valve 85 extending from the macrodrip chamber and tubing 90 containing an internal one way valve 95 extending from the microdrip chamber, flow control devices 60 and 70 on each of tubes 80 and 90, a clamp 100 on tube 80, a junction 110, a feed tube 120, and an intravenous catheter (not shown in the figures) connected to the feed tube 120. The entire packaged set can be sterilized by commonly used procedures. When the kit is needed, the sterile package is opened by the user and system is operated in manner described herein.

Flow Characteristics of the Infusion System

FIG. 5 demonstrates the flow characteristics of the infusion system. For these experiments, the spike connector 130 of the supply tube assembly 30 was inserted into a 1000 ml IV bag filled with 0.9% NaCl solution, elevated at 190 cm (spike connector level) above the ground and suspended at this height on an IV holder. The air-fluid level in the bag was kept at approximately 100 cm above the presumed infusion site. The IV tubing (3 meters long) was of a type customarily used in clinical practice. The flow rates were estimated by weighing the fluid collected from the infusion system at 60 second intervals. The flow rates were estimated using IV catheters of predefined size (22 Gauge, 20 Gauge or 18 Gauge). The measurements were performed using a laboratory electronic weighing scale, which was re-calibrated after every individual measurement (Mettler Toledo, Model B502, Switzerland). The measurements were done in triplicates and the mean values are included in FIG. 5.

When the microflow path 55 is used, the maximum achievable flow rate was reasonably similar regardless of the internal diameter of the IV catheter (22 Gauge, 20 Gauge and 18 Gauge catheters are used in these measurements), not exceeding 30 ml/min. This is in sharp contrast with a measured flow rate of a regular 15 drop/ml infusion system, where the flow rate is over 75 ml/min if the roller clamp is in the open position. Hence, distractions occurring during different medical procedures can easily lead to administration of inappropriate quantities of IV fluids if a conventional macrodrip infusion set (most commonly used during administration of anesthesia and surgery) is used.

Numerous modifications and variations in practice of the invention are expected to occur to those skilled in the art upon consideration of the foregoing detailed description of the invention. Consequently, such modifications and variations are intended to be included within the scope of the following claims.

What is claimed is:

1. An infusion system for intravenous administration of fluid to a patient from a fluid reservoir comprising:

a supply tube assembly effective for dividing a flow of fluid from the fluid reservoir into a macroflow path and a microflow path;

a dual-sight drip chamber, the dual-sight drip chamber comprising a macrodrip chamber and a microdrip chamber;

a flow control device effective for regulating flow of fluid in the macroflow path and a flow control device effective for regulating flow of fluid in the microflow path;

a clamp effective for stopping the flow of fluid in the macroflow path; and a junction effective for receiving and joining the macroflow path and microflow path into a single flow.

2. The infusion system of claim 1, wherein the fluid being administered to the patient is an anesthetic.

3. The infusion system of claim 1, wherein the flow of fluid in the microflow path is about 0.5 ml/min. to about 28 ml/min.

4. The infusion system of claim 1, wherein the flow of fluid in the macroflow path is about 4 ml/min. to about 75 ml/min.

5. A sterile and disposable kit for the intravenous administration of fluid to a patient, the kit comprising:

a supply tube assembly effective for dividing a flow of fluid from a fluid reservoir into a macroflow path and a microflow path;

a dual-sight drip chamber, the dual-sight drip chamber comprising a macrodrip chamber for receiving a macroflow path and a microdrip chamber for receiving a microflow path;

a tube extending from the macrodrip chamber and a tube extending from the microdrip chamber;

a flow control device on the tube extending from the macrodrip chamber and a flow control device on the tube extending from the microdrip chamber;

a clamp on the tube extending from the macrodrip chamber;

a junction effective for receiving and joining the tube extending from the macrodrip chamber and the tube extending from the microdrip chamber;

a supply tube extending from the junction; and an intravenous catheter.

6. The kit of claim 5, wherein the fluid being administered to the patient is an anesthetic.

* * * * *